(12) United States Patent
Ark et al.

(10) Patent No.: US 6,190,314 B1
(45) Date of Patent: Feb. 20, 2001

(54) COMPUTER INPUT DEVICE WITH BIOSENSORS FOR SENSING USER EMOTIONS

(75) Inventors: Wendy S. Ark; D. Christopher Dryer, both of Mountain View, CA (US)

(73) Assignee: International Business Machines Corporation, Armonk, NY (US)

( * ) Notice: Under 35 U.S.C. 154(b), the term of this patent shall be extended for 0 days.

(21) Appl. No.: 09/116,063

(22) Filed: Jul. 15, 1998

(51) Int. Cl.⁷ ........................................................ A61B 5/00
(52) U.S. Cl. ........................ 600/300; 600/595; 600/587; 704/270; 463/36
(58) Field of Search ..................................... 600/300, 301, 600/544–547, 595, 500, 481–486, 513, 587; 128/900, 903–905, 920–925; 704/270; 463/35–36; 345/156

(56) References Cited

U.S. PATENT DOCUMENTS

| | | | |
|---|---|---|---|
| 5,676,138 | * 10/1997 | Zawilinski | 600/300 |
| 5,720,619 | 2/1998 | Fisslinger | 434/336 |
| 5,741,217 | 4/1998 | Gero | 600/547 |
| 5,990,866 | * 11/1999 | Yollin | 345/157 |
| 6,026,322 | * 2/2000 | Korenman et al. | 600/547 |

* cited by examiner

Primary Examiner—Cary O'Connor
Assistant Examiner—Michael Astorino
(74) Attorney, Agent, or Firm—John L. Rogitz

(57) ABSTRACT

A method and system for correlating physiological attributes including heart rate, temperature, general somatic activity (GSA), and galvanic skin response (GSR) to N emotions of a user of a computer input device, such as a mouse. Sensors are in the mouse to sense the physiological attributes, which are correlated to emotions using a correlation model. The correlation model is derived from a calibration process in which a baseline attribute-to-emotion correlation is rendered based on statistical analysis of calibration signals generated by users having emotions that are measured or otherwise known at calibration time. A vector in N dimensions, representative of a subject user's emotions, is output for subsequent subject users whose emotions are sought to be known, with the baseline being the reference in the N-dimensional space of the vector.

19 Claims, 3 Drawing Sheets

COMPUTER INPUT DEVICE WITH BIOSENSORS FOR SENSING USER EMOTIONS

BACKGROUND OF THE INVENTION

1. Field of the Invention

The present invention relates generally to computer input devices, and more particularly to input devices that can sense physiological conditions of a user.

2. Description of the Related Art

People's emotions affect their performance in undertaking many tasks, including computer-related tasks. For example, a person who is agitated or angry is less likely to perform at an optimum level when operating a computer than is a person who is calm. Furthermore, a person's emotional state can be projected onto his or her computer; consequently, an otherwise "insensitive" computer might exacerbate, e.g., a person's anger or frustration.

With this in mind, the present invention understands that it can be important to know the emotional state of a computer user. With a knowledge of a user's emotional state, the present invention recognizes that it is possible to alter a computer's responses to user inputs as appropriate for the user's emotional state, thereby promoting the user's efficiency. Indeed, it can be important to know the emotional state of a person who is operating an instrument, such as a vehicle, that is not typically thought of as being computerized but that incorporates computers, to thereby promote the operator's efficiency or to warn an operator when his or her emotional state is less than optimum for operating the instrument.

When something stimulates an emotion in a person, the person's autonomic nervous system is affected, and in turn the autonomic nervous system affects the person's pulse, certain glands, and certain involuntary actions, collectively referred to herein as "physiological attributes". Accordingly, an understanding of a person's emotions can be gained by measuring certain of the person's physiological attributes, such as pulse and temperature.

It happens that many of these physiological attributes can be measured by sensors that touch the person. Thus, the present invention recognizes that an opportunity exists to non-invasively and unobtrusively measure physiological attributes of a computer user by providing biosensors in a computer input device, such as a mouse, that the user would be expected to routinely manipulate.

Unfortunately, prior devices that incorporate biosensors do not recognize the above-mentioned considerations and thus do not adequately address understanding the emotional state of a user. For example, U.S. Pat. No. 5,741,217 provides a galvanic skin response (GSR) sensor in a mouse to cause music to be played in response to the sensor, but the '217 patent does not correlate a physiological attribute directly to an emotional state. On the other hand, U.S. Pat. No. 5,720,619 teaches using biosensors to control a displayed visual "aura" in a computer game, but like the '217 patent, the '619 patent does not appear to recognize the desirability of correlating physiological attributes directly to a user's emotional state.

Fortunately, the present invention recognizes that it is possible to provide an unobtrusive, flexible, robust system and method for measuring physiological attributes of a computer user and then correlating the attributes to an emotional state that can be useful for a wide variety of purposes. Specifically, in a calibration group of people physiological attributes can be mapped or correlated to emotions by recording multiple physiological attributes along with, e.g., accompanying facial expressions or other expression of emotion, to render a baseline emotion correlation model. We have discovered that if a sufficient number of particularly selected physiological attributes are measured in subsequent subject computer users, using the baseline correlation model the emotional states of the users can be known and expressed in a functionally useful way.

SUMMARY OF THE INVENTION

A method is disclosed for correlating physiological attributes of a computer user to emotions when the user touches a computer input device. The method includes establishing baseline physiological signals that are representative of respective physiological attributes. Also, the method includes using the baseline physiological signals to statistically derive at least one correlation model. The correlation model correlates one or more physiological signals to one or more emotions. Subsequent physiological signals that are generated when a subject user touches the computer input device are received and, based on the correlation model, correlated to one or more emotions of the subject user.

In another aspect, a system includes a computer input device configured for engagement with a computer for inputting data to the computer. The system includes at least one input surface on the computer input device and configured for receiving a user signal, preferably a tactile signal, with the tactile signal being converted to an electrical signal for communication of the electrical signal to the computer. Also, the system includes one or more sensors on the computer input device for sensing one or more physiological attributes of a user when a user manipulates the input surface. As disclosed in detail below, the sensors generate respective physiological signals. A correlation element receives the physiological signals from the sensors and correlates the physiological signals to one or more emotions.

Preferably, the sensors include a heart rate sensor, a galvanic skin response (GSR) sensor, and a temperature sensor. Also, the system includes a computer for determining at least one of: a pressure on the input surface, and a speed of the input device relative to a stationary surface for deriving a general somatic activity (GSA) signal therefrom. The computer implements the correlation element, which includes logic means for establishing a baseline relationship between the physiological signals and the emotions, and logic means for using the baseline relationship to correlate the physiological signals to one or more of N emotions, wherein N is an integer.

In still another aspect, a computer program device includes a computer program storage device readable by a digital processing apparatus, and a program means is on the program storage device. The program means includes instructions that are executable by the digital processing apparatus for performing method steps for correlating physiological signals to emotions. The method steps that are performed include receiving one or more physiological signals from a computer input device that are generated as a result of a user touching the computer input device, and then correlating the physiological signals to one or more emotions. The computer program device can be combined with a general purpose computer.

The details of the present invention, both as to its structure and operation, can best be understood in reference to the accompanying drawings, in which like reference numerals refer to like parts, and in which:

DETAILED DESCRIPTION OF THE PREFERRED EMBODIMENTS

Figure 1:
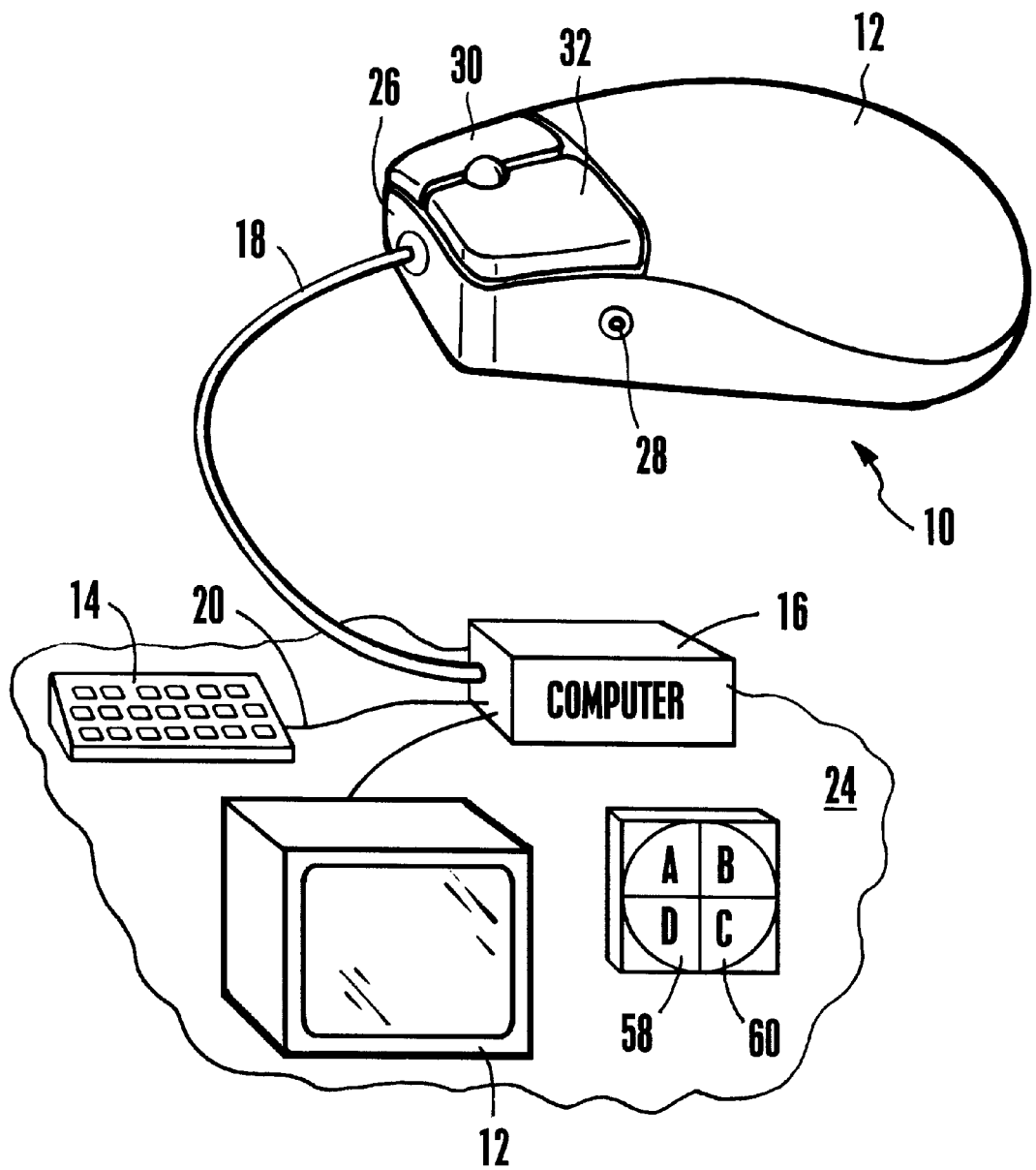
FIG. 1 is a schematic diagram of the present system for correlating physiological attributes of a computer user to an emotional state of the user.

Referring initially to FIG. 1, a system is shown, generally designated 10, which includes one or more input devices, such as a mouse 12 and a keyboard 14, for manipulation of the input devices to input data to a computer 16 via respective input cables 18, 20. The computer 16 in turn can output data to one or more output devices such as a monitor 22, and the computer 16 with input and output devices are supported on a surface 24.

The computer of the present invention can be a desktop computer such as a personal computer or laptop computer made by International Business Machines Corporation (IBM) of Armonk, N.Y. Alternatively, the computer of the present invention may be any computer, including computers sold under trademarks such as Apple, or other equivalent devices, including game computers. Additionally, input devices and output devices other than those shown can be used. For example, the computer 16 can be associated with one or more trackballs, keypads, joysticks, and voice activated input devices. Indeed, the present input device can be a wrist rest, watch band, and even a steering wheel or gear shift of a vehicle that communicates with a computer onboard a vehicle. The computer 16 can output data to a data storage device, a printer, or a computer network. Communication in the system 10 can be via electric cords or wireless technology.

In the particular embodiment shown, the mouse 12 includes one or more input surfaces for receiving user tactile signals that are converted to electrical signals for communication of the electrical signals to the computer 16. For example, the mouse 12 can include a button 26 that can be depressed by a user to generate a "click". The user signal need not be tactile, however. For example, the user signal can be a voice-generated sonic signal.

In accordance with the present invention, the mouse 12 includes plural biosensors for sensing respective physiological attributes of a user when the user manipulates the input surface 26 or otherwise generates a user signal. As disclosed in greater detail below, the biosensors generate respective physiological signals that represent respective physiological attributes of the user. It is to be understood that if desired, other input devices, such as the keyboard 14, or a camera, or a voice-activated device, or an optical sensor, can include the biosensors of the present invention.

In the preferred embodiment, the biosensors include a heart rate sensor 28 positioned on the side of the mouse 12 where the thumb of a right-handed user would normally rest. In this embodiment, the heart rate sensor 28 is an infrared sensor including a light emitting diode and associated phototransistor for reading blood flow in a capillary of that portion of the user's hand that contacts the heart rate sensor 28. More specifically, the LED emits light that is reflected by a capillary and detected by the phototransistor, for conversion into a pulse rate signal. Alternatively, a sonic heart rate sensor can be used and incorporated in the system 10.

Furthermore, a galvanic skin response (GSR) sensor includes a GSR electrode 30 that is disposed on the input surface 26 for generating a signal representative of the GSR of that portion of the user's hand that contacts the GSR electrode 30. Moreover, a temperature sensor includes a temperature electrode 32 that is disposed on the mouse 12 for generating a signal representative of the temperature of that portion of the user's hand that contacts the temperature sensor 32. In one preferred embodiment, the temperature electrode 32 is electrically connected to a thermistor chip made by Toko and marketed under the trade name "TK11041", with the thermistor chip generating a temperature signal. Alternatively, an optical (infrared) temperature sensor can be used and incorporated on, e.g., the mouse 12.

Figure 2:
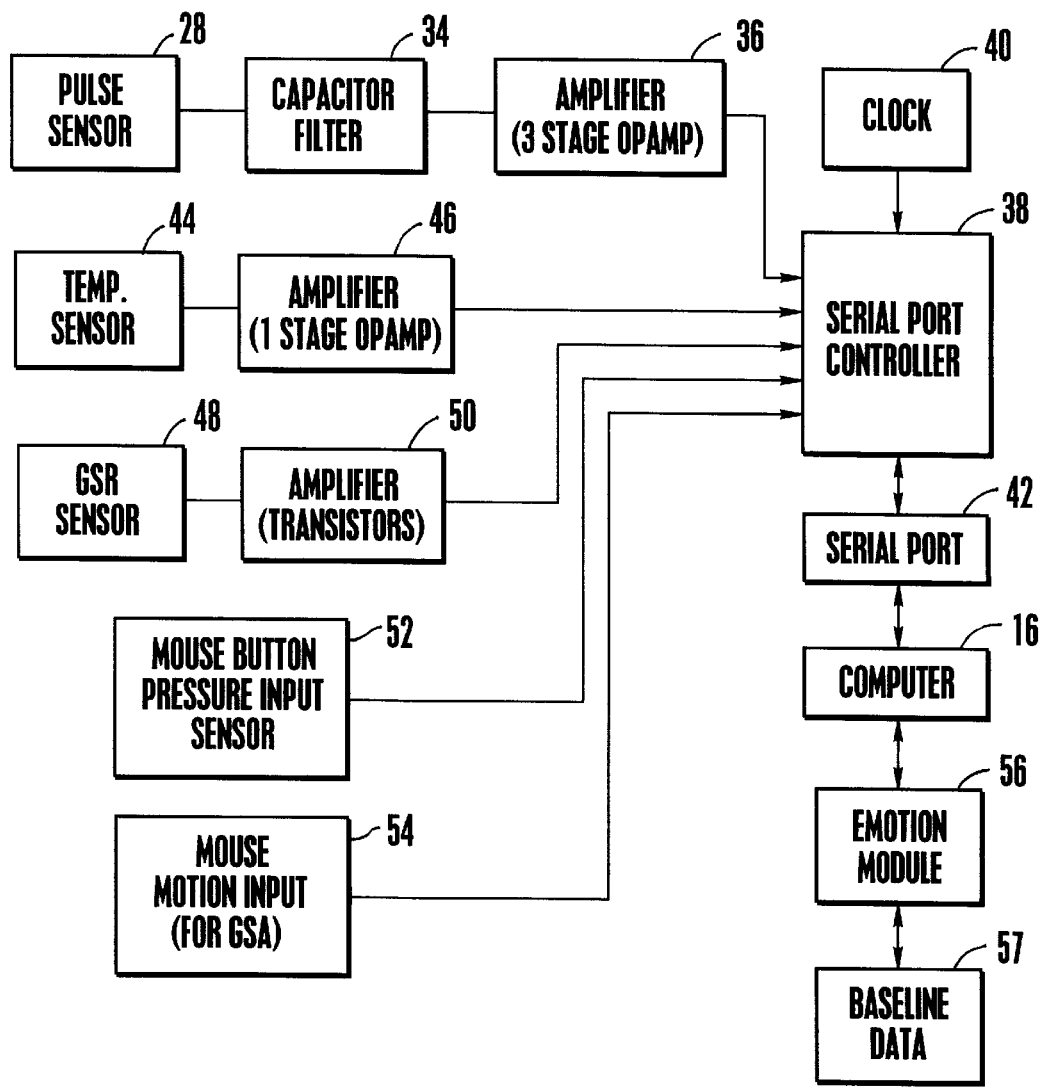
FIG. 2 is a block diagram of the electrical components of the system.

FIG. 2 shows additional details of the preferred embodiment. The heart rate sensor 28 is connected to a capacitor filter 34 to remove high frequency components from the heart rate signal from the sensor 32. In turn, the capacitor filter 34 is connected to a heart rate signal amplifier 36 which can be, e.g., a three stage operational amplifier. The amplified heart rate signal is then sent to a serial port controller chip 38, which uses a timing signal from a clock 40 to control communications to the computer 16 through a serial port 42 of the mouse 12 in accordance with principles well known in the art. In one embodiment, the serial port controller chip 42 is a type PIC16C71-04/JW(18) chip.

Also, a temperature sensor 44, which includes the temperature electrode 30 shown in FIG. 1, generates a signal representative of a user's temperature. This signal is amplified by a temperature signal amplifier 46 and then sent to the serial port controller chip 38. In one preferred embodiment, the temperature signal amplifier 46 includes a one stage operational amplifier.

Moreover, a galvanic skin response (GSR) sensor 48, which includes the GSR electrode 32 shown in FIG. 1, generates a signal representative of a user's GSR. The GSR signal is amplified by a GSR signal amplifier 50 and then sent to the serial port controller chip 38. In one preferred embodiment, the GSR signal amplifier 50 includes plural transistors.

In addition to the above-disclosed physiological signals, the present invention envisions using a general somatic activity (GSA) signal in determining a user's emotional state. In one embodiment, GSA is determined by sensing the pressure with which a user depresses a button, such as the input surface 26, and/or by determining how fast and how frequently the user moves the mouse 12 across the stationary surface 24. As recognized by the present invention, the higher the pressure and the faster the user moves the mouse 12, the higher the GSA signal. The relationship between pressure, mouse speed, and GSA output can be linear if desired.

Accordingly, a pressure sensor 52 can be mounted on the mouse 12 to sense the pressure with which a user depresses the input surface 26. Also, the standard mouse motion input 54, used by the computer 16 for data input purposes, can also be used alone or in combination with the pressure signal from the pressure sensor 52 to render a GSA signal. Both of these signal can be amplified and sent to the serial port controller 38, for association of the signals to a GSA signal by the computer 16, or the pressure signal and mouse motion signal can be associated with a GSA signal inside the mouse 12, for subsequent communication of the GSA signal to the serial port controller 38.

In accordance with the present invention, the computer 16 accesses an emotion module 56 that can be executed by the computer 16 to undertake the inventive logic disclosed below in detail. As shown in FIG. 2 and as disclosed in greater detail below, the emotion module 56 can access electronically-stored baseline data 57 in undertaking the present inventive logic. The baseline data 57 can include the below-disclosed discriminate functions as well as baseline emotion data from the calibration steps below.

It is to be understood that the control components such as the emotion module 56 are executed by logic components such as are embodied in logic circuits or in software contained in an appropriate electronic data storage, e.g., a hard disk drive and/or optical disk drive, that are conventionally coupled to the computer 16. Or, the control components can be embodied in other logical components such as a computer diskette 58 shown in FIG. 1. The diskette 58 shown in FIG. 1 has a computer usable medium 60 on which are stored computer readable code means (i.e., program code elements) A–D.

The flow charts herein illustrate the structure of the emotion module of the present invention as embodied in computer program software. Those skilled in the art will appreciate that the flow charts illustrate the structures of logic elements, such as computer program code elements or electronic logic circuits, that function according to this invention. Manifestly, the invention is practiced in its essential embodiment by a machine component that renders the logic elements in a form that instructs a digital processing apparatus (that is, a computer) to perform a sequence of function steps corresponding to those shown.

In other words, the emotion module 56 may be a computer program that is executed by a processor within the computer 16 as a series of computer-executable instructions. In addition to the drives mentioned above, these instructions may reside, for example, in RAM of the computer, or the instructions may be stored on a DASD array, magnetic tape, electronic read-only memory, or other appropriate data storage device. In an illustrative embodiment of the invention, the computer-executable instructions may be lines of compiled $C^{++}$ compatible code.

Figure 3:
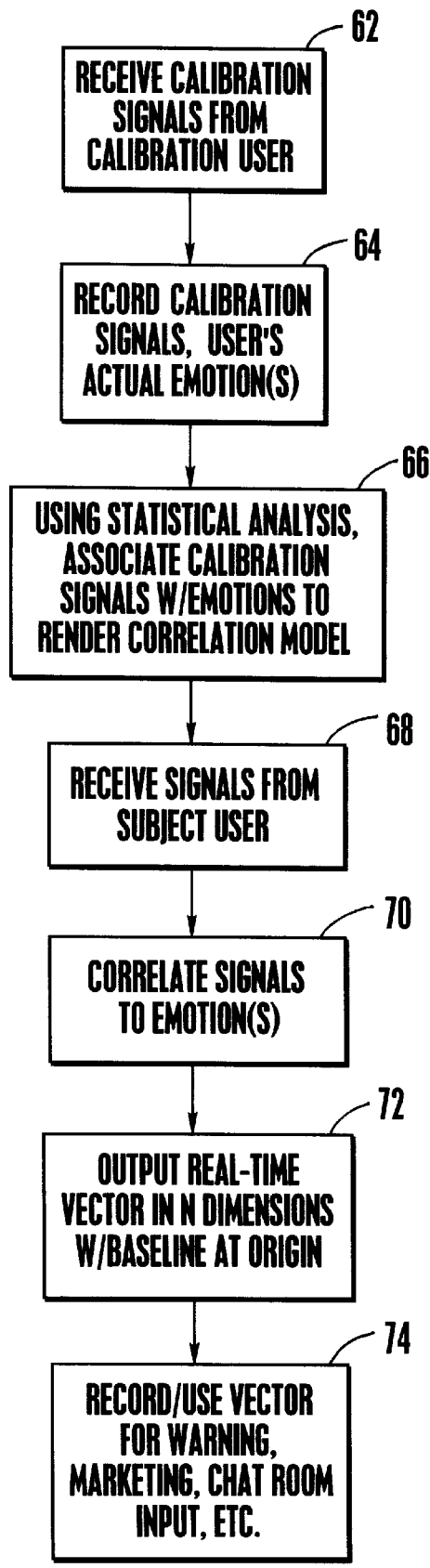
FIG. 3 is a flow chart showing the logic of the present method and system.

FIG. 3 shows the logic of the present invention. Commencing at block 62, calibration pulse, temperature, GSR, and GSA signals are received from the mouse 12 when one or more calibration users manipulate the mouse 12. These calibration signals are recorded and associated with the calibration user's actual emotions at block 64. In other words, the physiological signals are assessed and recorded along with the actual emotional state of the calibration user at the time the physiological signals are generated.

To do this, stimuli can be presented to the calibration user to evoke the desired emotion. In the presently preferred embodiment, the calibration user is asked to assume facial expressions for each emotion sought. In a particularly preferred embodiment, N emotions are sought, and the presently preferred emotions, along with the corresponding physiological signals, are recorded at block 64. In one exemplary embodiment, the emotions include anger, disgust, fear, joy, surprise, and sadness (N=6). Other emotions can be selected if desired. We have found that the above-mentioned combination of four physiological signals, a relatively precise correlation to one of the six emotions can be made. Moving to block 66, the relationship between each set of calibration physiological signals and the associated emotion is determined using statistical analysis techniques known in the art. For example, the relationship between each set of calibration physiological signals and the associated emotion can be determined using multidimensional scaling, factor analysis, and, when the emotions sought are undefined apriori, clustering. When the emotions sought are defined apriori, connectionist models can to be used to determine the relationship between each set of calibration physiological signals and the associated emotion.

In the preferred embodiment, however, discriminate function analysis is used in accordance with principles known in the art to determine a baseline relationship, that is, the relationship between each set of calibration physiological signals and the associated emotion to render the baseline data 57 shown in FIG. 2. To be included in the discriminant function analysis, the proportion of each signal's emotion-specific variance (that is not accounted for by other non-excluded signals) to total variance must exceed a criterion proportion, which in the preferred embodiment is 0.001 (i.e., one part per thousand). After any signals are excluded from the analysis, all signals are analyzed simultaneously to describe the baseline relationship by a number of discriminant functions that is equal to either one less than the number of emotions sought (i.e., that is equal to N−1) or that is equal to the number of physiological signals used, whichever is less.

Having calibrated the system 10, the logic moves to block 68 to receive physiological signals from a subject user whose emotional state is sought but unknown. At block 70, the physiological signals from the subject user are correlated to one of the "N" emotions using the baseline relationships (i.e., the discriminate functions) generated at block 66. Thus, block 70 establishes a correlation element for receiving the physiological signals from the sensors of the system 10 and correlating the physiological signals to one or more emotions.

Next, at block 72 the correlated emotion can be expressed as a real-time emotion vector in "N" dimensions, with the baseline data 57 establishing the origin of the vector space. The emotion vector is then recorded at block 74 for any number of uses, including input to a computer operating system to cause the operating system to, e.g., delay requests for data when the user is in a negative emotional state. Or, the computer operating system can be made to give higher priority than it otherwise would to user-defined tasks in response to particular emotions, as represented by the emotion vector.

Still again, the presently derived emotion vector can be used as an input to a vehicle or computer warning device to warn the subject user of an undesired emotional state. When incorporated in a vehicle, the present sensors can be mounted on the steering wheel or gear shift lever. Or, the sensors can be mounted on a telephone handset for recording a user's response to a telemarketing approach. Yet again, the emotion vector can be used as input to a computer chat room or computer game to vary the speed and skill level of the game in accordance with the emotion vector.

While the particular COMPUTER INPUT DEVICE WITH BIOSENSORS FOR SENSING USER EMOTIONS as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art. For example, physiological attributes other than those discussed above, e.g., blood oxygen level, blood pressure, camera-detected facial expression, and voice volume and stress level for voice-activated input devices, can be sensed and correlated to an emotional state of a user. The scope of the present invention accordingly is to be limited by nothing other than the appended claims, in which reference to an element in the singular means "at least one" unless otherwise recited.

What is claimed is:

1. A system including a computer input device configured for engagement with a computer for inputting data to the computer, comprising:

at least one input surface on the computer input device and configured for receiving a user signal, the user signal being converted to an electrical signal for communication of the electrical signal to the computer;

one or more sensors on the computer input device for sensing one or more physiological attributes of a user when a user manipulates the input surface, the one or more sensors generating respective physiological signals; and a correlation element for receiving the physiological signals from the one or more sensors and correlating the physiological signals to one or more emotions.

2. The system of claim 1, wherein the sensor is a heart rate sensor.

3. The system of claim 1, wherein the sensor is a galvanic skin response sensor.

4. The system of claim 1, wherein the sensor is a temperature sensor.

5. The system of claim 1, further comprising a computer for determining at least one of: a pressure on the input surface, and a speed of the input device relative to a stationary surface for deriving a general somatic activity signal therefrom.

6. The system of claim 1, wherein the sensor is a first sensor, and the computer input device further includes at least a second sensor, the first and second sensors being selected from the group of sensors including: heart rate sensors, galvanic skin response sensors, and temperature sensors.

7. The system of claim 6, further comprising a third sensor on the input device, the third sensor being selected from the group of sensors including: heart rate sensors, galvanic skin response sensors, and temperature sensors.

8. The system of claim 7, further comprising a computer for determining at least one of: a pressure on the input surface, and a speed of the input device relative to a stationary surface for deriving a general somatic activity signal therefrom, the physiological signals including the general somatic activity signal, a GSR signal, a temperature signal, and a heart rate signal.

9. The system of claim 8, wherein the computer implements the correlation element, the correlation element including:

logic means for establishing a baseline relationship between the physiological signals and the emotions;

logic means for using the baseline relationship to correlate the physiological signals to one or more of N emotions, wherein N is a positive integer.

10. A computer program device comprising:

a computer program storage device readable by a digital processing apparatus; and a program means on the program storage device and including instructions executable by the digital processing apparatus for performing method steps for correlating physiological signals to emotions, the method steps comprising:

receiving one or more physiological signals from a computer input device, the physiological signals being respectively representative of physiological attributes of a user, the physiological signals being generated as a result of a user touching the computer input devices; and correlating the physiological signals to one or more emotions.

11. The computer program device of claim 10, wherein the physiological signals include two or more of: a heart rate signal, a temperature signal, a general somatic activity, and a galvanic skin response signal.

12. The computer program device of claim 10, wherein the method steps further comprise:

establishing a baseline relationship between the physiological signals and the emotions; and using the baseline relationship to correlate the physiological signals to one or more of N emotions, wherein N is a positive integer.

13. The computer program device of claim 12, wherein the method steps further comprise:

in response to the correlating step, generating a vector in N dimensions relative to the baseline relationship.

14. The computer program device of claim 12, wherein the establishing step includes:

receiving plural calibration signals from one or more calibration users;

associating the calibration signals with emotions of the calibration users; and based on the associating step, rendering the baseline relationship using one or more statistical analyses.

15. The computer program device of claim 12, in combination with one or more a computers.

16. A method for correlating physiological attributes of a computer user to emotions when the user touches a computer input device, comprising:

establishing one or more baseline physiological signals, the physiological signals being representative of respective physiological attributes;

using the baseline physiological signals to statistically derive at least one correlation model, the correlation model correlating one or more physiological signals to one or more emotions;

receiving subsequent physiological signals generated when a subject user touches the computer input device; and based on the correlation model, correlating the subsequent physiological signals to one or more emotions of the subject user.

17. The method of claim 16, further comprising correlating the subsequent physiological signals to one or more of N emotions, wherein N is a positive integer.

18. The method of claim 17, further comprising, in response to the correlating step, generating a vector in N dimensions relative to the baseline relationship.

19. The method of claim 18, wherein the physiological signals include two or more of: a heart rate signal, a temperature signal, a general somatic activity, and a galvanic skin response signal.

* * * * *